United States Patent [19]

Buckle et al.

[11] Patent Number: 5,532,170
[45] Date of Patent: Jul. 2, 1996

[54] PROCESSING ANALYTICAL REAGENTS

[75] Inventors: Philip E. Buckle, Chatteris; Denise V. Pollard-Knight, St Albans, both of United Kingdom

[73] Assignee: Fisons plc, Ipswich, England

[21] Appl. No.: 104,076

[22] PCT Filed: Mar. 9, 1992

[86] PCT No.: PCT/GB92/00413

§ 371 Date: Aug. 6, 1993

§ 102(e) Date: Aug. 6, 1993

[87] PCT Pub. No.: WO92/15882

PCT Pub. Date: Sep. 17, 1992

[30] Foreign Application Priority Data

Mar. 9, 1991 [GB] United Kingdom ............. 9105031

[51] Int. Cl.$^6$ .............................................. G01N 33/531
[52] U.S. Cl. ................... 436/527; 436/525; 436/532; 436/533; 436/823; 530/391.1
[58] Field of Search ........................ 436/527, 525, 436/532, 823, 533; 530/334, 391.1

[56] References Cited

U.S. PATENT DOCUMENTS 4,529,712   7/1985   Jou et al. ................. 436/519

FOREIGN PATENT DOCUMENTS 0396116   11/1990   European Pat. Off. .
0403960   12/1990   European Pat. Off. .
PCT/US88/
01501   11/1988   WIPO .

OTHER PUBLICATIONS

"Facile preparation and some applications of an affinity matrix with a cleavable connector arm containing a disulfide bond," *Preparative Biochemistry*, 17(2), 121–141 (1987).

*Primary Examiner*—Mary E. Ceperley
*Attorney, Agent, or Firm*—Marshall, O'Toole, Gerstein, Murray & Borun

[57] ABSTRACT

A method of preparing functionalized particles including (a) treating an activated substrate (CPG) with a bifunctional cross-linking agent containing a cleavable bond so as to immobilize the cross-linking agent, (b) conjugating an activated particle (P) with the immobilized cross-linking agent, and (c) cleaving the cleavable bond so as to separate the particle (P) from the substrate (CPG). The functionalized particles subsequently can be conjugated to biologically active molecules for use in assay methods.

9 Claims, 4 Drawing Sheets

PROCESSING ANALYTICAL REAGENTS

This invention relates to a method for the preparation of functionalised particles for use in assay techniques.

A number of different instrumental techniques have been suggested for the determination of chemical and biochemical analytes in solution. Many of these have involved the immobilisation of a binding partner for the analyte on a surface, eg of glass or metal, and then bringing the solution containing the analyte into contact with the surface. Some change in a property of that surface, eg refractive index, due to binding of the analyte with the immobilised binding partner is then monitored, eg by evanescent wave or surface plasmon resonance techniques. The magnitude of this change gives a qualitative and/or quantitative indication of the presence of analyte in the sample.

Especially where the analyte is a relatively small molecule, eg a hapten, such methods may be unreliable since the change in surface property brought about by binding of the analyte may be relatively minor. Also, these methods may not achieve the sensitivity of conventional detection techniques.

One approach to this problem which is well known is to conjugate analyte molecules or specific binding partners of the analyte (or analogues of either thereof) with a larger particle and to use these conjugates in competition or displacement assays. Broadly speaking the change in surface property occurring on association or disassociation of a conjugate with the surface is greater than that which would occur with non-conjugated species and the sensitivity of the device is thereby increased.

In the preparation of biomolecule conjugates to particles, it is generally necessary to limit the number of biomolecules attached to each particle. This is certainly the case in sensitivity enhancement for sensor techniques which detect changes in refractive index and thickness using enhancer probes, such as particles to which biomolecules are attached, for a displacement or competition assay. If there is more than one biomolecule attached to each probe then multiple attachment points may occur and displacement can be difficult due to the high affinity. This is illustrated in FIG. 1. FIG. 1(a) shows particles P to which DNA molecules D are attached. The particles P are bound to a surface S by means of (i) single and (ii) multiple binding of the DNA molecules D to oligonucleotides N immobilised on the surface S. FIG. 1(b) shows analogous binding of particles P via biomolecules B attached to the particles P and antibodies A immobilised on the surface S.

Similarly in a competition assay, if more than one biomolecule is attached to an enhancer probe then the sensitivity of the assay is significantly reduced. Adsorption at low concentrations of the biomolecules can be used to limit the number attached to the particle; however, this is difficult to control, is not reproducible and attachment via adsorption may inactivate the biomolecule.

We have now devised a method of preparing functionalised particles for use in assay techniques which overcomes or substantially mitigates the above disadvantages.

According to the invention, there is provided a method of preparing functionalised particles, which comprises a) treating an activated substrate with a bifunctional cross-linking agent containing a cleavable bond so as to immobilise the cross-linking agent, b) conjugating an activated particle in the form of a bead with a diameter of 5–1000 nm with the immobilised cross-linking agent, and c) cleaving the cleavable bond so as to separate the particle from the substrate.

The method according to the invention is advantageous inter alia in that a) Very low numbers of biomolecules per particle may be obtained.

b) By packing the support in a column, the process may be automated thus reducing preparation times considerably.

c) Solvents and unreacted reagents may be removed easily without complex separations.

d) Since all unreacted particles are washed off prior to cleavage, only modified particles will be obtained.

e) Particles modified with different chemistries may be obtained using similar prepacked columns.

Figure 1A:
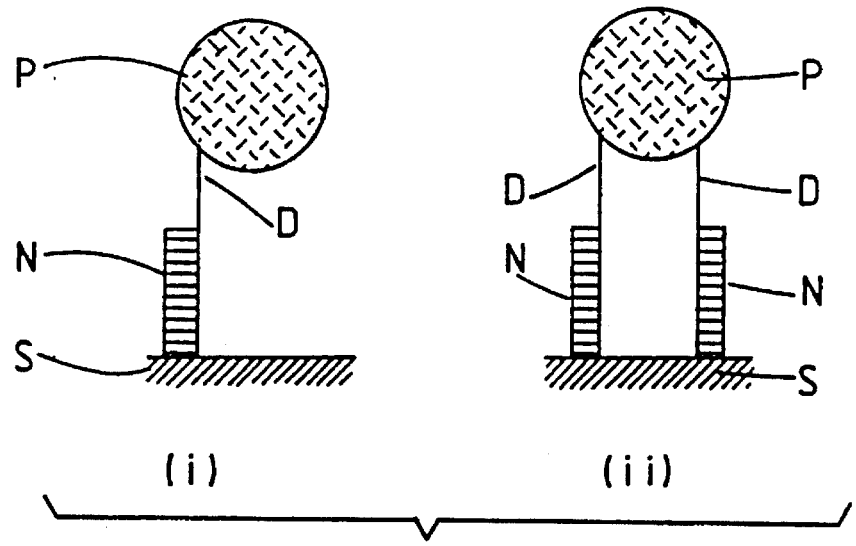
FIG. 1A shows particles P to which DNA molecules D are attached, wherein the particles P are bound to a surface S by means of (i) single and (ii) multiple binding of the DNA molecules D to oligonucleotides N immobilized on the surface S.
Figure 1B:
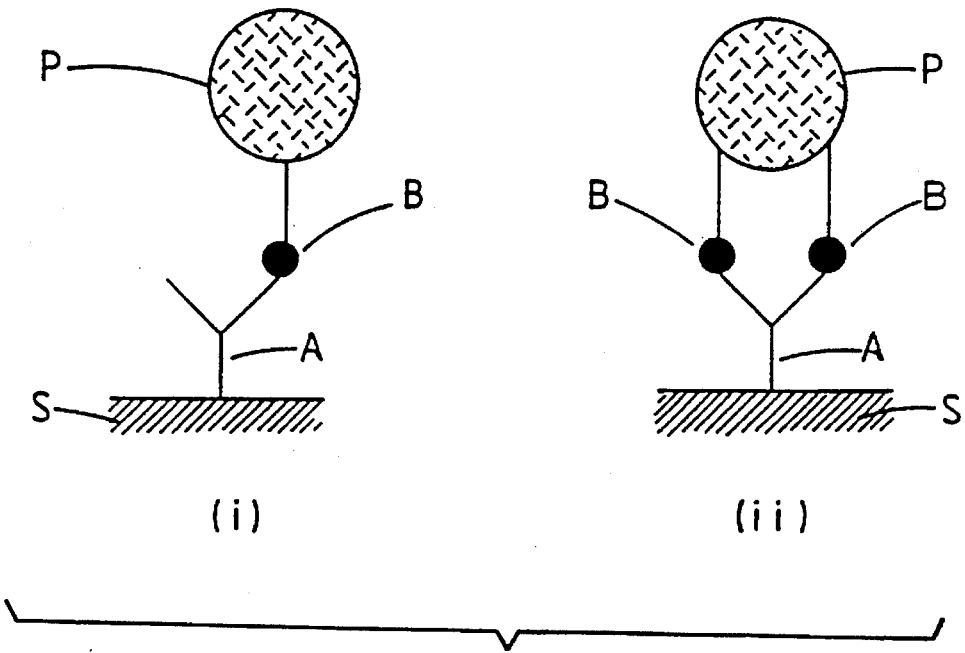
FIG. 1B shows analogous binding of particles P via biomolecules B attached to the particles P and antibodies A immobilized on the surface S.

The substrate may take any convenient form, but is preferably in the form of relatively large beads chemically modified such that cleavable molecules may be employed to cross-link to suitably chemically modified particles. Examples of particles for the substrate include controlled pore glass (CPG) and polystyrene having amino, carboxyl or hydroxyl groups. The beads may be packed into a column, the various processing stages being carried out by passing the various reagents through the column. The beads typically have a diameter of 5–200 µm.

The cross-linking agent may be any reagent capable of coupling the substrate to the particle. The cross-linking agent is preferably a homo-bifunctional cross-linker. The cleavable bond may be any bond which is readily cleavable without disrupting unnecessarily any other chemical bonds in the system. The cleavable bond is most preferably a disulphide bond. The preferred cross-linking agent is 3,3'-dithiobis(sulpho succinimidyl propionate) (DTSSP).

Examples of particles in the form of small beads include polystyrene, colloidal gold, titanium dioxide and polyvinyl chloride which may contain a fluorescent or absorbing dye. Such beads typically have a diameter of 5–1000nm.

Where the cleavable bond is a disulphide bond, the bond is preferably cleaved with a cleaving agent such as dithiothreitol (DTT) or 2-mercaptoethanol. These reagents will produce particles having a thiol group that may be attached to biomolecules. Peptides may be cleaved by proteases such as chymotrypsin, trypsin, pepsin, papain etc.

Between the major processing stages it may be necessary to allow sufficient time to elapse for the various reactions to go to completion. Following each processing step, it may also be necessary to wash off excess reagent. Following conjugation of the activated particle with the immobilised cross-linking agent, it may also be necessary to cap any unreacted functional groups using conventional reagents. Amino groups may, for example, be capped using acetic anhydride.

Following cleavage of the cleavable bond, the functionalised particles are collected and may then be used for conjugation to other molecules. A coupling reagent is normally used to effect the covalent binding between the particle and the other molecule. Such coupling reagents include hydrazides, azides, cyanogen bromide, N,N-o-phenyldimaleimide, m-maleimidobenzoyl-N-hydroxysuccinimide ester and the like. The choice of coupling agent will of course depend on the particular particle and other molecule concerned.

In bringing about the covalent binding between the particle and the other molecule, the coupling reagent is normally added to a solution or mixture of the particle and/or other molecule, the concentration of the coupling reagent varying with the particular system involved. After incubation, typically for several hours, the other molecule is added and the mixture further incubated. The conjugate is then isolated using known techniques.

In another approach, the functionalised particle is contacted with other molecules which have previously been immobilised on a solid support, eg a similar activated substrate to that used in the preparation of the functionalised particle.

The conjugate is then typically diluted in a suitable buffer, such as carbonate-bicarbonate, to a concentration which will generally be in the range of 10 to 200 ng/ml, eg about 100 ng/ml. Other buffers can of course be used, eg glycine buffer pH 9.5, and other dilutions, eg 50 ng/ml. The solution may then be contacted with the surface of an analytical device having immobilised upon it a specific binding partner for the other molecule. Contact is maintained for a sufficient time to permit the conjugate to bind to the immobilised species. After binding is complete, the surface is washed free of unbound conjugate. This washing can be effected using any suitable solution, eg phosphate buffered saline, or distilled water. Several washings may be necessary to ensure that no unbound conjugate is left in contact with the surface which can then be dried, eg by air drying or freeze drying, and stored for future use.

Figure 2:
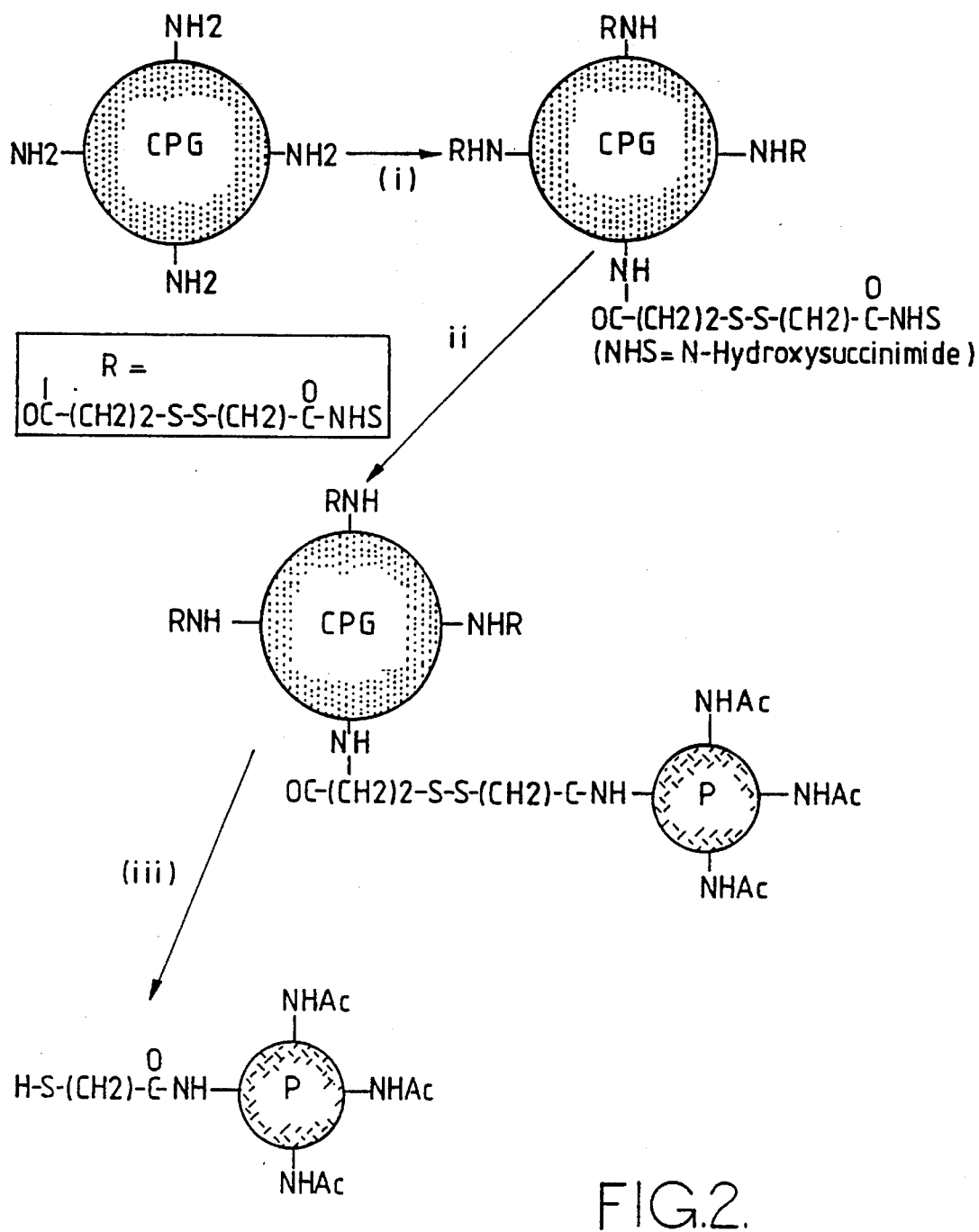
FIG. 2 is a schematic diagram of the preparation of thiol-modified particles.
Figure 3:
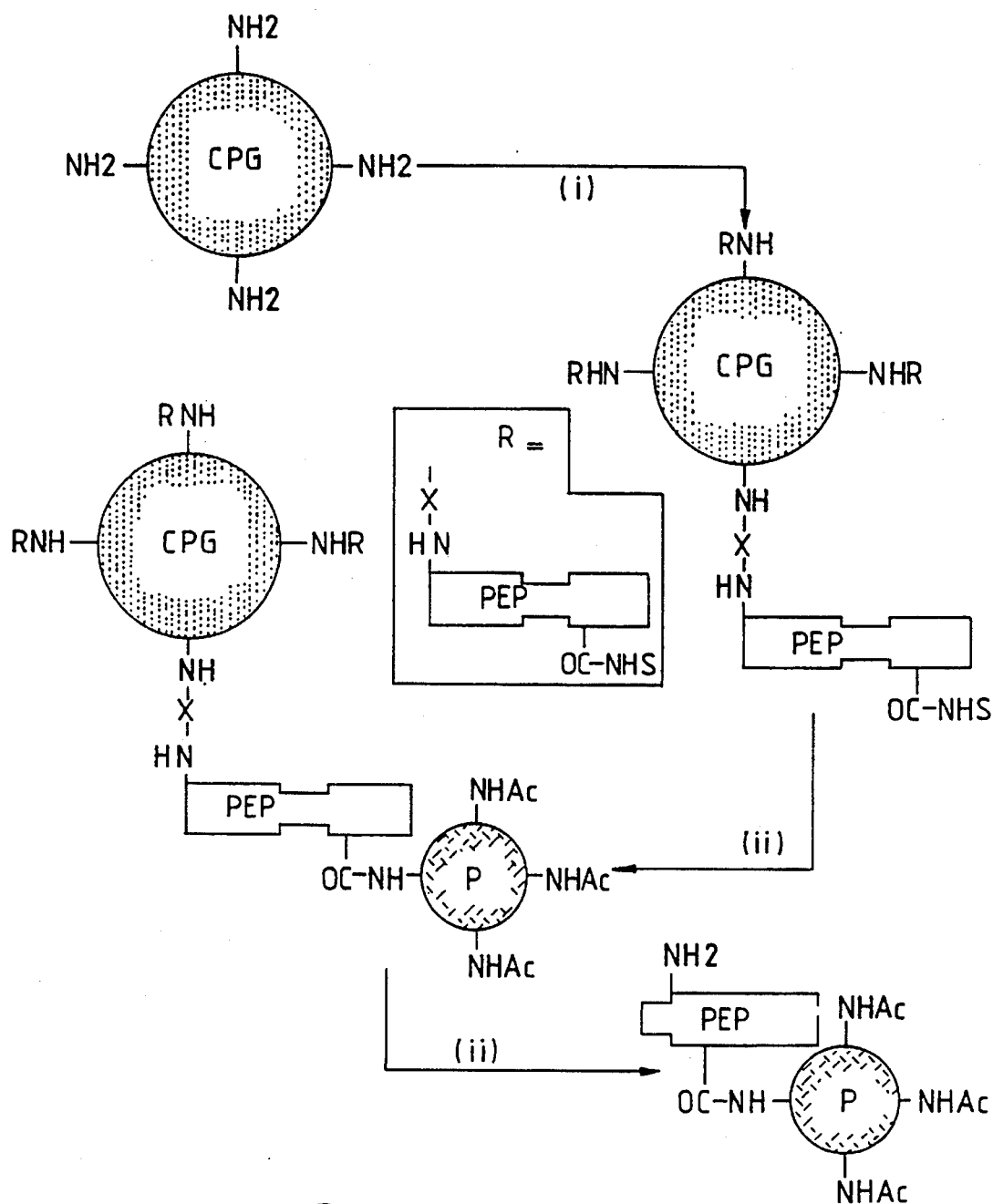
FIG. 3 is a schematic diagram of the preparation of peptide-modified particles.
Figure 4:
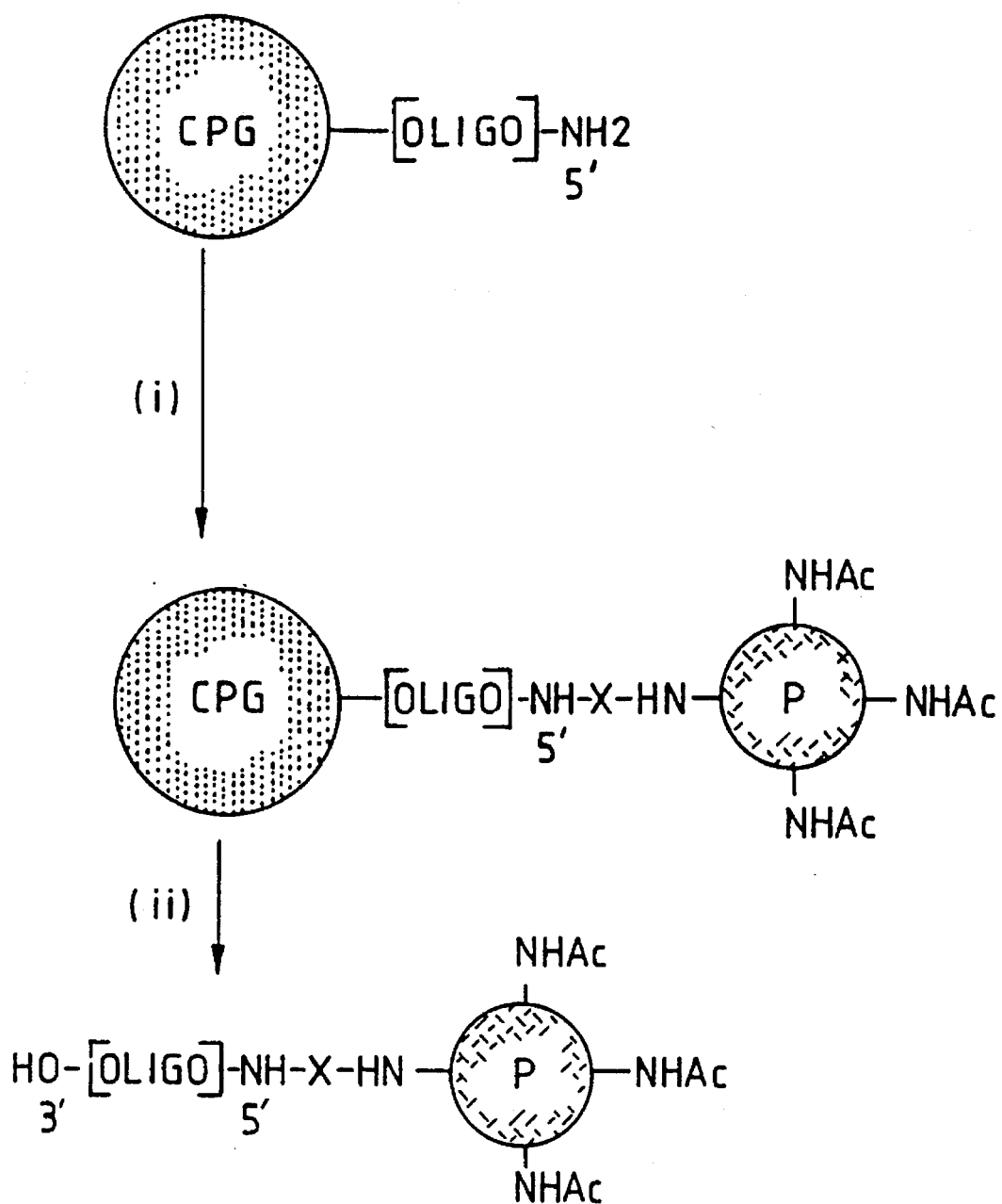
FIG. 4 is a schematic diagram of the preparation of oligonucleotide-modified particles.

The invention will now be described in more detail, by way of illustration only, with reference to the following Examples and FIGS. 2 to 4 in which:

FIG. 2 is a schematic diagram of the preparation of thiol-modified particles,

FIG. 3 is a schematic diagram of the preparation of peptide-modified particles, and FIG. 4 is a schematic diagram of the preparation of oligonucleotide-modified particles.

EXAMPLE A

Preparation of Amino-Modified Glass Balls

A thin layer of glass balls (CPG, 75–150 μm) was placed in a large petri dish, and 1 ml of 3-aminopropyltrimethoxysilane in a smaller petri dish. Both dishes were placed for 30 minutes in an oven at 140° C. under vacuum.

The vacuum was released, the balls shaken, and a further 1 ml of the aminosilane added. Again, both dishes were placed in the oven at 140° C. under vacuum for 30 minutes. The vacuum was released and the balls allowed to cool.

EXAMPLE B1

Preparation of Thiol-Modified Latex Particles

Step (i) of FIG. 2:

A small glass column was packed with 1 g of amino-modified CPG balls (CPG) prepared as described in Example A. The balls (CPG) were washed with 250 mM sodium phosphate buffer, pH 7.4. 10 mM DTSSP in sodium phosphate buffer, pH 7.4, was added and incubated for 1 hour.

Step (ii) of FIG. 2:

The column was washed with one volume of sodium phosphate buffer and 0.5% amino-latex (100 nm) particles (P) in sodium phosphate buffer and 0.1% GAFAC added and incubated for one hour. The column was washed with 5 volumes of buffer and 50 mM acetic anhydride in 250 mM sodium phosphate buffer added and incubated for one hour.

Step (iii) of FIG. 2:

The column was washed with 5 volumes of buffer, pH 7.4, and the latex particles (P) cleaved and eluted with 50 mM dithiothreitol (DTT).

EXAMPLE B2

Preparation of Thiol-Modified Latex Particles

Amino-modified CPG (prepared as in Example A) was stirred in pH 9 buffer in a small reaction vessel (5 ml) into which was introduced an excess of DTSSP. After reaction, the excess DTSSP was removed by successive buffer washes, and the modified CPG resuspended in the same buffer.

Amino-modified latex particle solution (100 nmparticles) was then introduced into the reaction vial and allowed to react with the stirred modified CPG. Unreacted latex was removed by washing and the resulting CPG-latex adduct transferred to a short column where it was equilibrated with a suitable buffer.

The latex was cleaved from the CPG using either DTT or 2-mercaptoethanol, the product being collected with the column eluate. The cleavage reagent was removed by gel filtration or membrane filtration.

This method is superior to that of Example B1 in that it prevents aggregation of the latex particles on top of the column due to the presence of residual cross-linkers or organic solvents.

EXAMPLE C1

Preparation of Peptide-Modified Particles

Step (i) of FIG. 3:

Amino-modified CPG balls (prepared as in Example A) are packed into a column, reacted with a cross-linker (X) and a peptide (PEP) amine, and the peptide carboxyl group activated.

Step (ii) of FIG. 3:

Amino-modified latex particles (P), prepared as in Example B, are added, excess particles washed off and free amines capped with acetic anhydride.

Step (iii) of FIG. 3:

The peptide (PEP) is cleaved by chemical or enzymatic cleavage and the peptide-modified particles eluted.

EXAMPLE C2

Preparation of peptide-Modified Particles—Improved Method

Complications may be encountered with the method of Example C1 since incomplete blocking of the thiol-modified latex beads may lead to cross-linking of bioactive molecules to different sites (eg amino and sulphydryl groups).

Since the thiol-modified latex has many more amino groups than thiol groups, reaction of the latex with a heterobifunctional cross-linker such as succinimidyl 4-[N-maleimidomethyl]cyclohexane-1-carboxylate (SMCC) will occur predominantly through the amino groups and not the desired thiol-maleimide coupling. This will lead to the undesirable formation of multiple protein binding sites on the latex particles.

If the cross-linker is first coupled to a protein molecule, a similar pair of reactions may occur. In this case, however, so that the subsequent attachment to the latex can be through the desired thiol-maleimide coupling, it is preferable that coupling of the protein to the cross-linker is via the protein amino group. This can be achieved by performing the reaction of protein and cross-linker (SMCC) at high pH, eg pH 9. The derivatised latex may then be coupled exclusively via the thiolmaleimide groups. Purification by gel filtration gives the required protein-labelled latex beads.

Using $^{125}$I labelled proteins, the number of protein molecules attached per latex bead may be quantified.

EXAMPLE D

Preparation of Oligonucleotide-Modified Particles

Step (i) of FIG. 4:

CPG beads with attached 5-amino-modified oligonucleotides (OLIGO) are prepared using a DNA synthesiser. The beads are reacted with a cross-linker (X) and then with amine-modified particles (P) prepared as in Example B. Unreacted particles are washed off and unreacted amines capped with acetic anhydride.

Step (ii) of FIG. 4:

The oligonucleotides (OLIGO) are cleaved from the beads (CPG) by ammonia cleavage.

We claim:

1. A method of conjugating a biomolecule with a particle in the form of a bead having a diameter of 5–1000 nm, which method comprises the steps of
   (a) treating an activated substrate with a bifunctional cross-linking agent containing a cleavable bond so as to immobilize the cross-linking agent,
   (b) conjugating the particle with the immobilized cross-linking agent,
   (c) cleaving the clearable bond so as to separate the particle from the substrate,
   (d) collecting the particle so released from the substrate, and
   (e) reacting the particle with the biomolecule.

2. A method as claimed in claim 1, wherein the substrate is in the form of beads of diameter of 5–200 μm.

3. A method as claimed in claim 1, wherein the substrate is in the form of beads of controlled pore glass (CPG) having amino groups.

4. A method as claimed in claim 1, wherein the cross-linking agent is homo-bifunctional.

5. A method as claimed in claim 1, wherein the cross-linking agent contains a disulphide bond.

6. A method as claimed in claim 1, wherein the cross-linking agent is 3,3'-dithiobis(sulphosuccinimidyl propionate).

7. A method as claimed in claim 1, wherein the particle is of a material selected from the group consisting of polystyrene, colloidal gold, titanium dioxide, and polyvinyl chloride.

8. A method as claimed in claim 1, wherein a coupling reagent is used to effect covalent binding between the particle and the biomolecule.

9. A method as claimed in claim 8, wherein the coupling reagent is selected from the group consisting of hydrazides, azides, cyanogen bromide, N,N-o-phenyldimaleimide and m-maleimido-benzoyl-N-hydroxysuccinimide ester.

\* \* \* \* \*

UNITED STATES PATENT AND TRADEMARK OFFICE
CERTIFICATE OF CORRECTION

PATENT NO. : 5,532,170

DATED : July 2, 1996

INVENTOR(S) : Philip E. Buckle et al.

It is certified that error appears in the above-identified patent and that said Letters Patent is hereby corrected as shown below:

Column 6, line 12, "clearable" should be --cleavable--.

Signed and Sealed this

Twenty-fourth Day of February, 1998

Attest:

BRUCE LEHMAN

Attesting Officer

Commissioner of Patents and Trademarks